US 6,695,830 B2

(12) United States Patent
Vigil et al.

(10) Patent No.: US 6,695,830 B2
(45) Date of Patent: Feb. 24, 2004

(54) METHOD FOR DELIVERING MEDICATION INTO AN ARTERIAL WALL FOR PREVENTION OF RESTENOSIS

(75) Inventors: Dennis M. Vigil, San Diego, CA (US); Robert E. Reiss, La Jolla, CA (US); Peter Barath, Oak Brook, IL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/778,594

(22) Filed: Feb. 7, 2001

(65) Prior Publication Data
US 2001/0041859 A1 Nov. 15, 2001

Related U.S. Application Data

(63) Continuation-in-part of application No. 09/232,392, filed on Jan. 15, 1999, now Pat. No. 6,210,392.

(51) Int. Cl.[7] .............................................. A61M 31/00
(52) U.S. Cl. ..................... 604/509; 604/104; 604/96.01; 606/194
(58) Field of Search ............................ 604/19, 27, 28, 604/48, 73, 93, 96.01, 97.01, 104, 105, 107, 500, 501, 507–509, 523, 103.03, 502, 181, 183, 164.01, 164.02, 103.07, 103.08; 606/191–198

(56) References Cited

U.S. PATENT DOCUMENTS

| | | | |
|---|---|---|---|
| 2,816,552 A | | 12/1957 | Hoffman |
| 3,593,713 A | | 7/1971 | Bogoff et al. |
| 3,635,223 A | | 1/1972 | Klieman |
| 3,993,538 A | | 11/1976 | Lebowitz et al. |
| 4,057,617 A | * | 11/1977 | Abramovici et al. ........... 424/1 |
| 4,140,126 A | | 2/1979 | Choudhury |
| 4,273,128 A | | 6/1981 | Lary |
| 4,318,400 A | | 3/1982 | Peery et al. |
| 4,441,509 A | | 4/1984 | Kotsifas et al. |
| 4,465,072 A | | 8/1984 | Taheri |
| 4,922,926 A | | 5/1990 | Hirschberg et al. |
| 5,009,659 A | | 4/1991 | Hamlin et al. |
| 5,030,201 A | | 7/1991 | Palestrant |
| 5,070,877 A | | 12/1991 | Mohiuddin et al. |
| 5,100,425 A | | 3/1992 | Fischell et al. |
| 5,112,305 A | * | 5/1992 | Barath et al. .................. 604/96 |
| 5,156,610 A | | 10/1992 | Reger |
| 5,196,024 A | | 3/1993 | Barath |
| 5,242,397 A | * | 9/1993 | Barath et al. .................. 604/96 |

(List continued on next page.)

FOREIGN PATENT DOCUMENTS

| | | | |
|---|---|---|---|
| DE | 3519626 A1 | 4/1986 | |
| EP | 0 399 712 | 11/1990 | |
| EP | 0 567 788 A1 | 3/1993 | |
| EP | 0 783 898 A1 * | 7/1997 | .......... A61M/25/10 |
| GB | 1547328 | 6/1979 | |
| JP | A-4-282146 | 10/1992 | |
| JP | A-6-098938 | 11/1993 | |
| WO | WO 94/09845 | 5/1994 | |
| WO | WO 94/23787 | 10/1994 | |
| WO | WO 00/41761 A1 | 7/2000 | |

Primary Examiner—Brain L. Casler
Assistant Examiner—Jennifer Maynard
(74) Attorney, Agent, or Firm—Kenyon & Kenyon

(57) ABSTRACT

A method for preventing a restenosis within a vessel wall requires a medicament be delivered at predetermined locations into the vessel wall and allowed to subsequently disperse in a predetermined pattern. To deliver the medicament, a catheter with an expanding member is advanced into the vasculature of a patient until the expanding member is located as desired. The expanding member is then expanded to force dispensers into the vessel wall to the proper depth. A medicament is then pumped through the dispensers to create a plurality of equally spaced, localized medicinal deliveries which subsequently disperse to medicate an annulus shaped volume within the vessel wall.

28 Claims, 11 Drawing Sheets

U.S. PATENT DOCUMENTS

| | | | | |
|---|---|---|---|---|
| 5,279,565 A | * | 1/1994 | Klein et al. | 604/105 |
| 5,282,785 A | | 2/1994 | Shapland et al. | |
| 5,286,254 A | | 2/1994 | Shapland et al. | |
| 5,295,962 A | | 3/1994 | Crocker et al. | |
| 5,306,250 A | | 4/1994 | March et al. | |
| 5,320,634 A | | 6/1994 | Vigil et al. | |
| 5,322,508 A | | 6/1994 | Viera | |
| 5,328,471 A | | 7/1994 | Slepian | |
| 5,336,178 A | * | 8/1994 | Kaplan et al. | 604/53 |
| 5,354,279 A | | 10/1994 | Hofling | |
| 5,364,356 A | | 11/1994 | Hofling | |
| 5,370,614 A | | 12/1994 | Amundson et al. | |
| 5,415,637 A | | 5/1995 | Khosravi | |
| 5,423,851 A | | 6/1995 | Samuels | |
| 5,459,240 A | * | 10/1995 | Foxwell et al. | 530/328 |
| 5,477,857 A | | 12/1995 | McAfee et al. | |
| 5,571,086 A | * | 11/1996 | Kaplan et al. | 604/96 |
| 5,599,306 A | | 2/1997 | Klein et al. | |
| 5,609,574 A | * | 3/1997 | Kaplan et al. | 604/53 |
| 5,611,767 A | | 3/1997 | Williams | |
| 5,620,687 A | * | 4/1997 | Hart et al. | 424/143.1 |
| 5,626,830 A | | 5/1997 | Sikorska et al. | |
| 5,667,764 A | | 9/1997 | Kopia et al. | |
| 5,681,281 A | * | 10/1997 | Vigil et al. | 604/96 |
| 5,693,029 A | | 12/1997 | Leonhardt | |
| 5,713,860 A | * | 2/1998 | Kaplan et al. | 604/96 |
| 5,713,863 A | * | 2/1998 | Vigil et al. | 604/104 |
| 5,746,716 A | * | 5/1998 | Vigil et al. | 604/97 |
| 5,772,629 A | * | 6/1998 | Kaplan et al. | 604/52 |
| 5,855,563 A | * | 1/1999 | Kaplan et al. | 604/49 |
| 5,858,990 A | * | 1/1999 | Walsh | 514/44 |
| 5,873,811 A | | 2/1999 | Wang et al. | |
| 5,873,852 A | * | 2/1999 | Vigil et al. | 604/52 |
| 5,941,868 A | * | 8/1999 | Kaplan et al. | 604/500 |
| 6,054,114 A | * | 4/2000 | Lansbury, Jr. et al. | 424/1.11 |
| 6,102,904 A | * | 8/2000 | Vigil et al. | 604/500 |
| 6,210,392 B1 | * | 4/2001 | Vigil et al. | 604/507 |
| 6,280,414 B1 | * | 8/2001 | Shah et al. | 604/104 |
| 6,413,203 B1 | | 7/2002 | Sahatjian | |

* cited by examiner

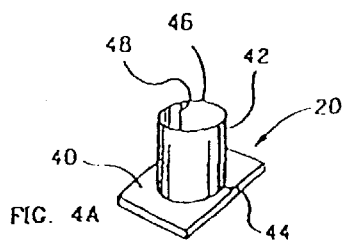
FIG. 4A
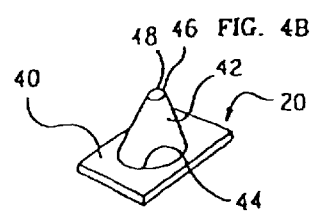
FIG. 4B
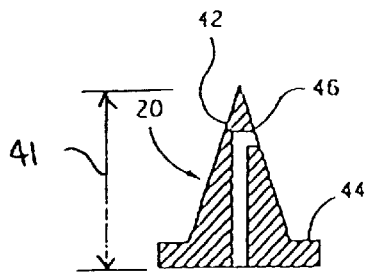
FIG. 5A
FIG. 5B
FIG. 5C
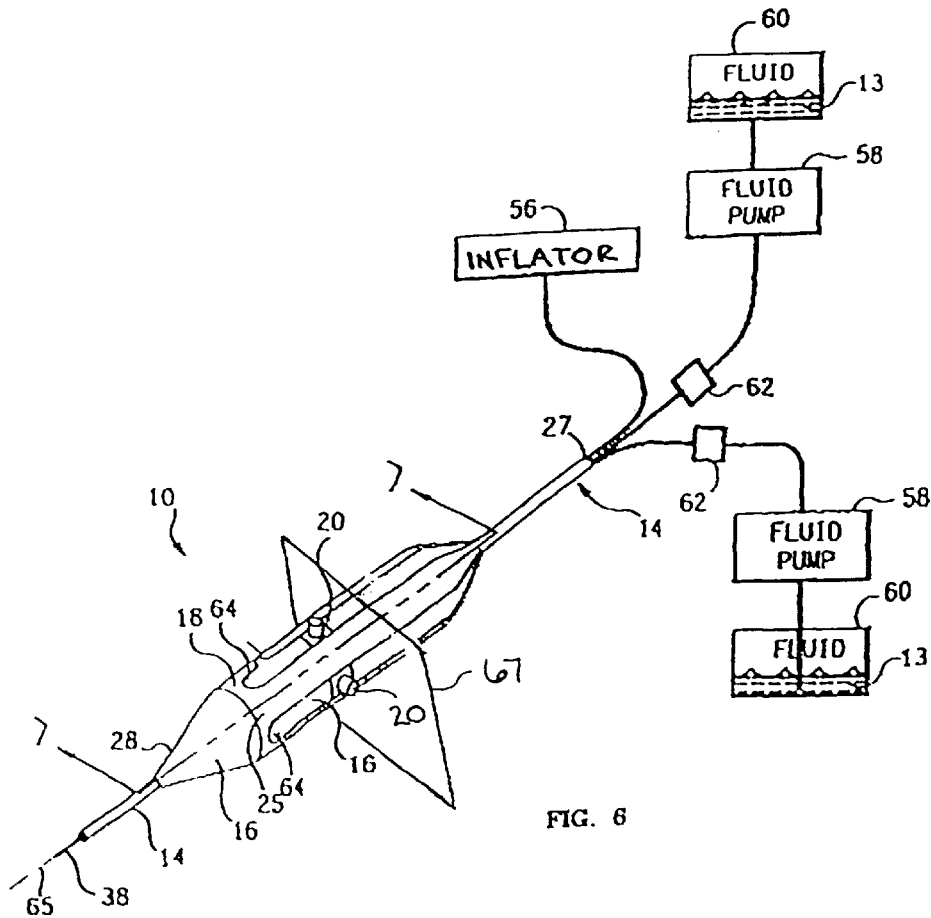
FIG. 6

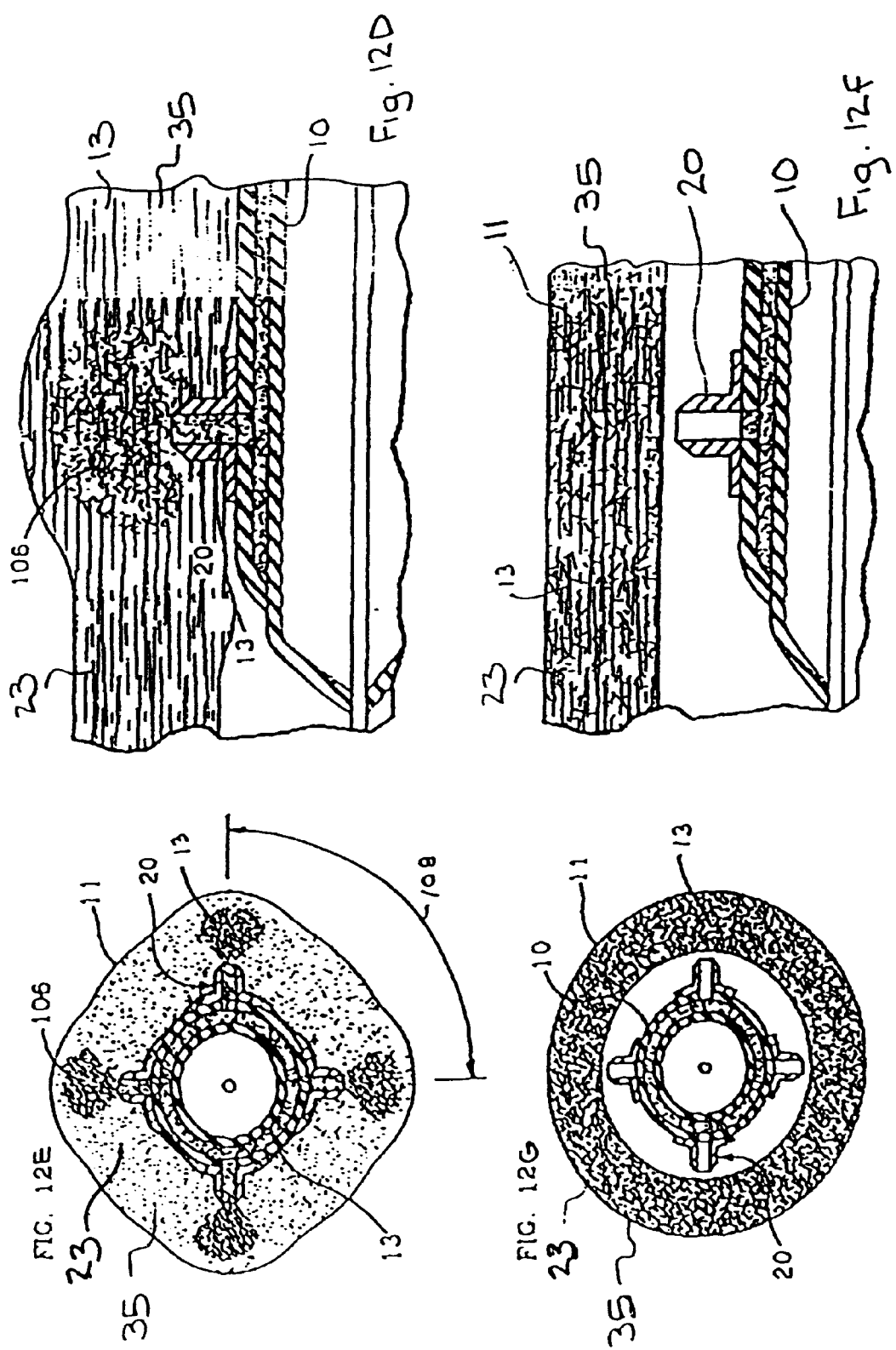

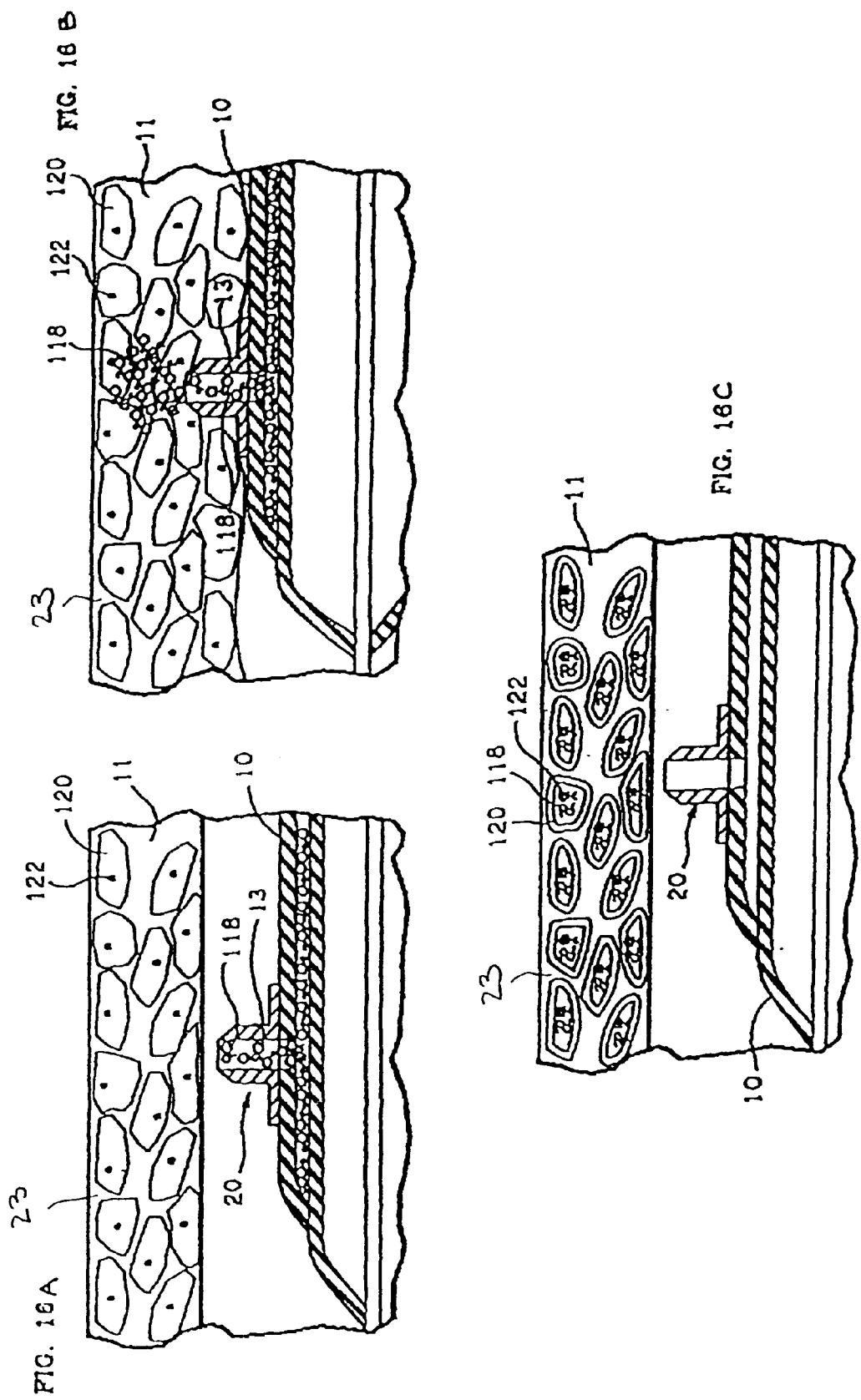

METHOD FOR DELIVERING MEDICATION INTO AN ARTERIAL WALL FOR PREVENTION OF RESTENOSIS

This application is a continuation-in-part of application Ser. No. 09/232,392, filed on Jan. 15, 1999, which is now U.S. Pat. No. 6,210,392. The contents of application Ser. No. 09/232,392 are incorporated herein by reference.

FIELD OF THE INVENTION

The present invention pertains generally to a method for treating the vessel of a patient. More specifically, the present invention pertains to a medical method for treating a vessel of a patient's cardiovascular system by injecting a fluid directly into the vessel wall. The present invention is particularly, but not exclusively, useful for preventing a restenosis by releasing a medicament at several predetermined locations within the vessel wall to circumferentially disperse the medicament in the vessel wall.

BACKGROUND OF THE INVENTION

Angioplasty is a widely used procedure for treating a stenosis within a body vessel such as a human artery. During an angioplasty procedure, a medical catheter having an inflatable balloon attached to a catheter shaft is advanced within the lumen of the body vessel until the balloon is adjacent to the stenosis. Next, the balloon is inflated causing the stenosis to compress into the vessel wall and the lumen of the vessel to dilate.

Although the angioplasty procedure is generally successful in dilating the lumen of the vessel and thereby allowing increased blood flow through the vessel, often times a restenosis occurs soon after the angioplasty procedure. It is widely recognized that the bodies response (inflammation) to tissue damage that occurs during the angioplasty procedure contributes to the restenosis. Several medicaments are known to be efficacious in the prevention of a restenosis if properly delivered near the site of the inflammation.

Heretofore, a number of devices have been suggested for use in conjunction with an angioplasty procedure to obviate a restenosis. For example, one such device utilizes a balloon to position a plurality of apertures against the vessel wall near the stenosis. After positioning the apertures, a medicament is released from the apertures, where the medicament contacts the endothelium layer of the vessel. Unfortunately, use of the aperture device generally results in an insufficient amount of medicament being delivered to the target area because a large portion of the released medicament does not penetrate the vessel wall, but rather, is washed away into the blood stream. Further, due to the toxic nature of some of the medicaments used in this procedure, the large portion of medicament entering the bloodstream can cause adverse health effects to the patient.

Also heretofore, devices capable of penetrating the wall of a vessel with a dispenser and releasing a medicament within the vessel wall have been disclosed. For example, U.S. Pat. No. 5,713,863, filed on Jan. 11, 1996 and entitled "Catheter With Fluid Medication Dispensers" and which is assigned to the same assignee of the present invention, discloses such a device.

It is to be appreciated that the use of devices with expanding members and penetrating dispensers will cause some trauma to the vessel wall. Specifically, as indicated above, dilation of the vessel lumen with a balloon or other expanding member is generally known to cause tissue injury to the vessel wall. Further, penetration of the vessel wall with a dispenser will certainly cause some injury to vessel wall tissue. Finally, the release of a medicament within the vessel wall will also cause some injury to the tissue of the vessel wall.

These various forms of tissue injury will trigger an inflammation response. As indicated above, this inflammation response is widely recognized to contribute to the restenosis of the vessel. It is also known that this inflammation response will cause localized changes near the injured tissue including increased permeability and increased blood flow. This localized increase in blood flow and permeability will generally increase the dispersion rate of medicaments released near an injury in a vessel wall.

For a medicament to be effective in preventing a restenosis it must be delivered to a prescribed area and in a prescribed dosage. As indicated above, the size, shape and location of the prescribed treatment area is dependent on the amount and location of tissue injury. On the other hand, the amount of tissue injury is dependent on a number of factors including the size of the balloon, the number of penetrating dispensers and the amount of medicament released. Further, the dispersion rate of the medicament will be affected by the amount of inflammation, the type of medicament, and the amount of medicament released. Consequently, all of these factors must be considered when determining the arrangement of the dispensers and the amount of medicament to be released at each dispenser that will result in a uniform dispersion of medication at the prescribed treatment area.

In light of the above, it is an object of the present invention to provide a method useful for preventing a restenosis caused by trauma to vessel tissue from an intravascular procedure. It is another object of the present invention to provide a method for preventing a restenosis in a vessel by delivering a medicament at predetermined locations within the vessel wall for dispersion into a prescribed shape that takes advantage of the increased medicinal dispersion rate due to the localized inflammation created by the procedure. It is yet another object of the present invention to prevent a restenosis by delivering a medicament at predetermined locations within a vessel wall to create a circumferential dispersion of the medicament within the vessel wall near a stenosis. Another object of the present invention is to safely deliver dangerous medicaments into a vessel wall while minimizing the amount of medicament which is washed away into the blood stream. Still another object of the present invention is to provide a method for treating a vessel which is easy to perform, safe, relatively simple, and inexpensive to perform.

SUMMARY OF THE PREFERRED EMBODIMENTS

The present invention is directed to a method for preventing a restenosis from occurring near the site of an intervascular catheter procedure such as a balloon angioplasty procedure. In accordance with the present method, the restenosis is prevented by medicating a prescribed treatment area within the vessel wall near the site of the angioplasty procedure. For the present method, a medicament known to prevent restenosis is delivered at predetermined locations within the vessel wall and allowed to subsequently disperse thereby medicating the prescribed treatment area. The delivery of the medicament can be accomplished either during the angioplasty procedure or shortly thereafter.

In accordance with the present method, first, the shape, size and location of the treatment area to be medicated is prescribed. For purposes of the present invention, the treatment area is generally a circumferentially shaped volume (or annulus) within the vessel wall near the site of the catheter procedure. For angioplasty procedures that dilate the lumen of the vessel near an existing stenosis, the present method contemplates medication of an annulus near the treated stenosis having a annulus length of approximately the size of the stenosis. Further, the prescribed annulus is preferably wholly contained within a particular vessel layer. For example, in the case of an arterial vessel, the particular vessel layer may be the intima or the media. Next, the delivery locations, delivery rates and delivery amounts are calculated after considering the dispersion rate of the medicament and the various factors that affect the dispersion rate such as the effect of inflammation. Once the delivery locations, rates and amounts are determined, the arrangement and size of the medicament dispensers can be determined and used to configure a catheter for delivering the medicament.

To deliver the medicament in accordance with the present method, a catheter with an expanding member, such as a balloon, is advanced along a catheter shaft within the lumen of a body vessel until the expanding member is located adjacent to the prescribed treatment area. A plurality of dispensers are mounted on the expanding member and an extracorporeal mechanism for pumping a medicinal fluid to the dispensers through a lumen in the catheter is provided. Importantly, in order to medicate an annulus within the vessel wall as contemplated by the present method, all of the dispensers are positioned on the expanding member in a plane oriented substantially perpendicular to the axis of the catheter shaft.

Once the expanding member is positioned adjacent to the treatment area, it can be activated to force the dispensers into the vessel wall. By the proper design and dimension of the expanding member and dispensers, the dispensers can be made to penetrate to the prescribed vessel layer. Once the dispensers have penetrated the vessel wall to the proper depth, a medicament can be selectively pumped through each dispenser for release at the predetermined locations. Preferably, the dispensers create a plurality of equally spaced localized medicinal deliveries which subsequently disperse to substantially medicate an annulus within the vessel wall. Simultaneously, the expanding member, which may be a balloon, can dilate the lumen of the vessel, thereby producing results similar to the balloon angioplasty procedure described above.

As provided below, the expanding member selectively and accurately controls the movement of the dispensers, and the medicament source selectively provides a pressurized supply of medicament to the dispensers. Thus, the expanding member mechanism which causes the dispensers to penetrate the vessel wall operates independently from the extracorporeal mechanism for pumping the medicinal fluid to the dispensers, thereby allowing greater freedom in medicinal delivery.

For the method of the present invention, the expanding member may include a balloon which is expandable from a contracted, first configuration to an expanded, second configuration. Preferably, the dispensers extend radially from the balloon and move with the balloon between the first configuration and the second configuration. This structure allows the dispensers to penetrate into a prescribed target vessel layer such as the intima or media for selective release of a medicament when the balloon is at the second configuration. When properly designed, this structure allows both the depth of penetration of the dispensers into the vessel wall and the force used to penetrate the vessel wall to be precisely controlled.

Further, for the method of the present invention, at least one fluid passageway provides for fluid communication between the medicament source and the dispensers. For example, the fluid passageway can include a flexible tubular sleeve which substantially encompasses and encloses at least a portion of an outer surface of the balloon. The medicament source can also include an extracorporeal fluid pump which is in fluid communication with the fluid passageway for selectively providing a pressurized supply of medicament from the medicament source to the dispensers.

Each dispenser can be a substantially tubular protrusion having an attachment end and a penetrating section for penetrating the wall of the vessel. The attachment end includes a base plate which mounts directly onto the tubular sleeve. In some of the devices disclosed herein for use in the present method, an open edge defines the penetrating section of the dispenser. In alternative devices useful for the present method and disclosed herein, each dispenser can include a porous section or an opening through the dispenser wall which defines the penetrating section.

Depending upon the medicament and the desired treatment, the medicament can be released while the dispenser penetrates the treatment area or there can be a time delay between the dispenser penetration and the release of the medicament from the dispensers.

An alternative structure for the expanding member may include a multilumen catheter, a grommet, a plurality of flexible tubes which connect the grommet to the catheter and a dispenser secured to each of the flexible tubes. The grommet is movable relative to the catheter to reposition the flexible tubes near the vessel wall.

Various medicaments can be used in the method of the present invention depending on the needs of the individual patient. As indicated above, a medicament suitable for the treatment of a stenosis or disease de novo, inhibiting a restenosis by minimizing the effects of a previous intravascular procedure and/or inhibiting a stenosis in a vessel may be used. For example, to inhibit a restenosis, the medicament may contain an anti-proliferative agent which inhibits the proliferation of smooth muscle cell growth in a vessel under certain pathological conditions. Further, medicaments which selectively kill rapidly dividing cells can also be used to inhibit the proliferation of smooth tissue growth. Other suitable medicaments can include anti-proliferative agents such as methotrexate, prednisone, adriamycin, mitomycin C, protein synthesis inhibitors, toxin fragments such as pseudomonas exotoxin (PE) or Ricin A (RA) Toxin, and radioactive isotopes such as $^{111}$Indium, $^{90}$Yttrium, $^{67}$Gallium, $^{99m}$Tc(Technetium 99), $^{205}$Thallium, and $^{32}$P (Phosphorous 32) radiopharmaceuticals. Alternatively, a medicament which stimulates the production of collateral vessels can be delivered to the target area by the present method. This provides preventative treatment for the patient by creating new collateral vessels in the event the original vessel develops a stenosis. A medicament which includes an angiogenis factor can be utilized for this purpose.

In order to decrease the amount of medicament washed away into the blood stream, a portion of the medicament could precipitate at approximately the vessel pH level of the vessel. Typically, the vessel pH is approximately 7. Thus, a medicament having a pH level of less than approximately 6 or greater than approximately 8 can be utilized. After the medicament is dispensed into the wall of the vessel, the medicament pH level approaches 7 and a portion of the medicament precipitates. For these purposes, the fluid can include a precipitator, an active component attached to or included within the precipitator and a carrier component which carries the precipitator and the active component. The precipitator precipitates in the wall of the vessel while the carrier component gets washed away into the blood stream. Because the active component is attached to or included within the precipitator, the active component of the fluid remains in the vessel wall. This minimizes the amount of the active component of the fluid medicament which is washed away into the blood stream. For these purposes, the active component of the medicament, for example, can include an anti-proliferative agent as discussed above. Alternatively, the precipitator and active component, for example, can include a radionuclide or radiopharmaceutical precipitate, such as gold colloidal, i.e. $^{198}$Au and $^{199}$Au, and/or an inorganic precipitate.

Additionally, the active component of the medicament can be designed to have a slow, time-release formulation so that the active component is released to the vessel wall over an extended period of time. Stated another way, the active component can biodegrade slowly over a period of time to gradually release the active component of the medicament into the vessel wall. A biodegradable polymer could be used to provide a control release formulation to the active component.

Alternatively, the medicament could include a binder secured to the active component of the medicament. The binder binds, attaches or crosslinks to at least a portion of the wall of the vessel. The binder can include a ligand which binds to a portion of the vessel wall such as collagen or the smooth muscle cell component of the vessel wall. This ensures that the bulk of the active component of the medicament remains in the vessel wall and minimizes the amount of the active component of the medicament which is washed away into the blood stream. Examples of ligands binding to the vessel wall components include PDGF receptors, adhesive molecules including but not limited to certain molecules of the integrin family, and receptors on activated platelets such as thrombin receptors. Alternatively, for example, phoshporous tridentate which binds to collagen can be utilized. Further, a binder that has a direct affinity to form ionic bonds, covalent bonds or Van der Waal attractions to the wall of the vessel or some component thereof can be used in the method of the present invention.

Further, a medicament for performing gene therapy on the vessel wall can be used. For example, the medicament could include either retroviral, adenoviral vectors or Adenovirus Associated Vectors (AAV) carrying the appropriate DNA payload for appropriate gene switching. The method of the present invention also allows for the use of medicaments which genetically alter the specific treatment site of the vessel without effecting the rest of the body. Additionally, the method of the present invention may be used to inject radioactive isotopes directly into the vessel wall.

BRIEF DESCRIPTION OF THE DRAWINGS

The novel features of this invention, as well as the invention itself, both as to its structure and its operation will be best understood from the accompanying drawings, taken in conjunction with the accompanying description, in which:

FIG. 4A is a perspective view of a first embodiment for a dispenser suitable for use in the present invention;

FIG. 4B is a perspective view of a second embodiment for a dispenser suitable for use in the present invention;

FIG. 5A is a side plan view of a third embodiment of a dispenser suitable for use in the present invention;

FIG. 5B is a side plan view of a fourth embodiment of a dispenser suitable for use in the present invention;

FIG. 5C is a side plan view of a fifth embodiment of a dispenser suitable for use in the present invention;

FIG. 6 is a perspective view of another embodiment of a device suitable for use in the present invention;

FIG. 12D illustrates a longitudinal cross-sectional view of the intima layer of the vessel wall after the fluid medicament has been injected into the vessel wall;

FIG. 12E is an axial cross-sectional view illustrating the intima layer of the vessel wall after the fluid medicament has been injected into the vessel wall;

FIG. 12F is a longitudinal cross-sectional view of a portion of the intima layer of the vessel and the device illustrating the fluid medicament after dispersion in the vessel wall;

FIG. 12G is an axial cross-sectional view of the intima layer of the vessel and the device illustrating the fluid medicament after dispersion in the vessel wall;

FIG. 15B is a longitudinal cross-sectional view of a portion of the vessel and the device showing the binder of an injected medicament binding to a portion of the vessel wall;

FIG. 16A is a longitudinal cross-sectional view of a portion of a vessel and device illustrating the cell genes of the vessel prior to penetration of the vessel with the dispenser;

FIG. 16C is a longitudinal cross-sectional view of a portion of the vessel and device illustrating the vessel wall after the injected virus genes have attacked and replaced the cell genes.

DESCRIPTION OF THE PREFERRED EMBODIMENTS

Figure 1A:
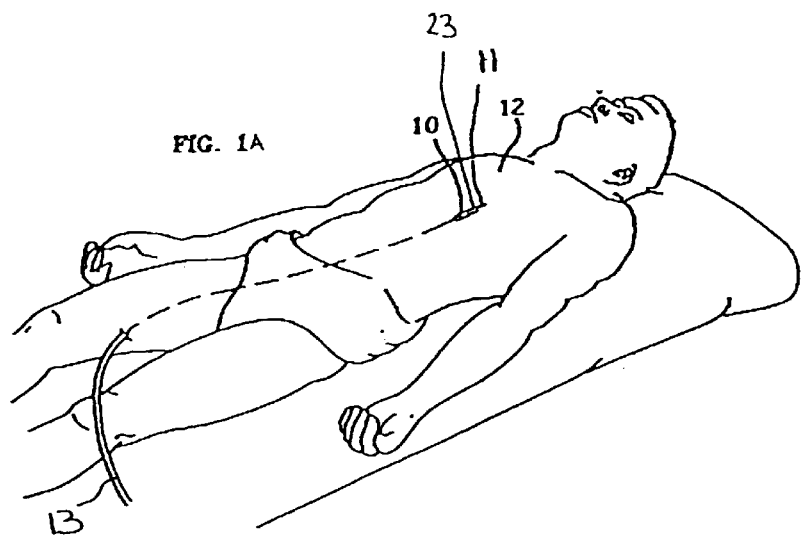
FIG. 1A is a perspective view of a patient with a device positioned in an artery of the patient in accordance with the method of the present invention.
Figure 1B:
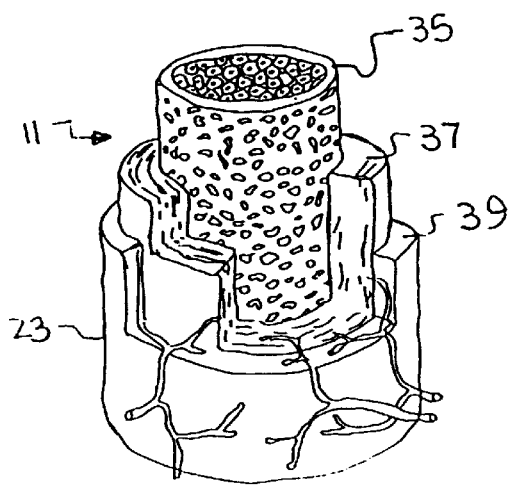
FIG. 1B is a perspective view of a portion of an artery of a patient showing the intima, media and adventitia layers.
Figure 1C:
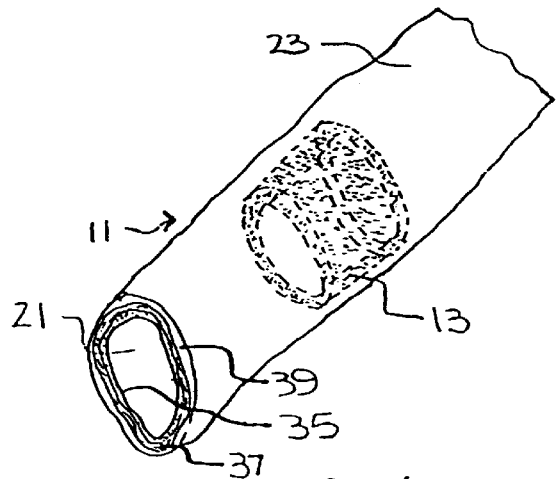
FIG. 1C is a perspective view of a portion of an artery of a patient showing a circumferential dispersement of a medicament (in phantom) in accordance with the method of the present invention.

Referring initially to FIG. 1A, a device 10 for injecting a fluid medicament 13 into a wall 23 of a living blood vessel 11 in accordance with the method of the present invention is shown positioned in an upper body, blood vessel 11 of a patient 12. It is to be appreciated that the present method can be used in arteries and other vessels throughout the body of the patient 12. FIG. 1B shows the wall 23 of an arterial blood vessel 11 having three layers of importance for the present invention, the intima 35, the media 37 and the adventitia 39. As shown in FIG. 1C, the intima 35 surrounds the lumen 21 of the blood vessel 11. Importantly, as provided in detail below, the device 10 when used in accordance with the method provided herein, allows for a substantially circumferential dispersion of the fluid medicament 13 within the wall 23 of the blood vessel 11, as shown in FIG. 1C. Further, in accordance with the present method, a circumferential dispersion of fluid medicament 13 can be made within one of the layers 35, 37, 39 of wall 23 of the blood vessel 11.

Figure 2:
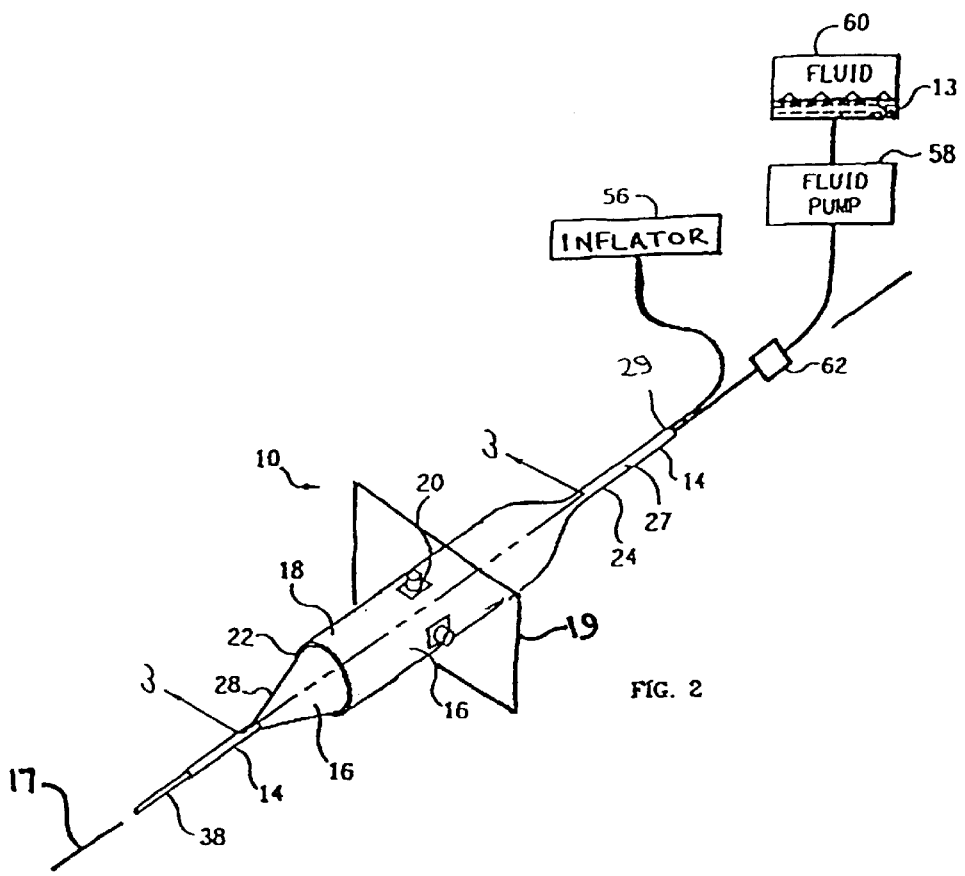
FIG. 2 is a perspective view of a device suitable for use in the method of the present invention.
Figure 3A:
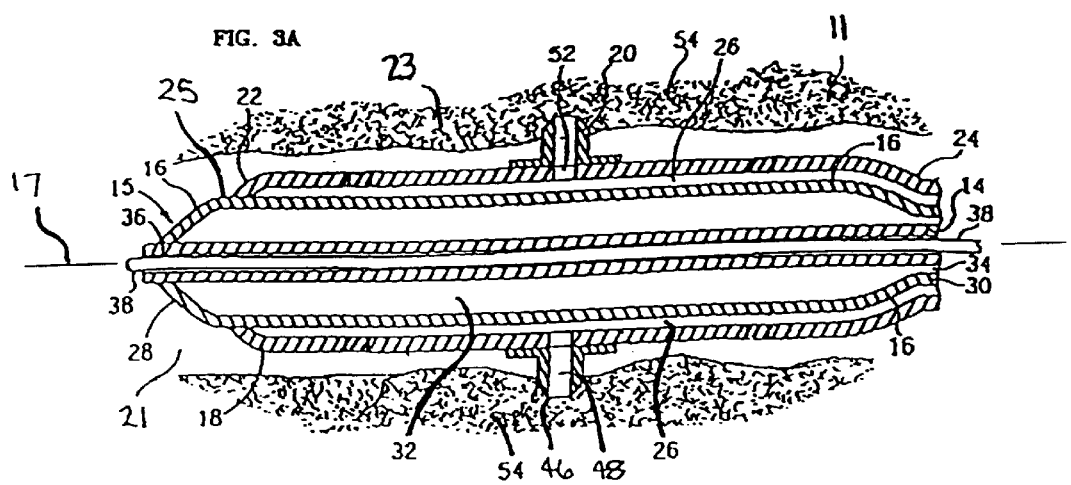
FIG. 3A is a cross-sectional view of the device of FIG. 2 as seen along line 3—3 in FIG. 2, positioned in an artery of a patient.

Referring to FIGS. 2 and 3A, a first version of a device 10 suitable for the method of the present invention includes a multi-lumen catheter 14, an expanding member 15 mounted thereon, a tubular sleeve 18 and a plurality of dispensers 20. Although FIGS. 2 and 3A show the expanding member 15 as an inflatable balloon 16, any expanding member known in the art may be used. The balloon 16 is inflatable and deflatable between a first, substantially deflated configuration and a second, substantially expanded configuration. The balloon 16, while in the second configuration, can be anywhere from partially inflated to fully inflated depending upon the size of the blood vessel 11. The balloon 16 and tubular sleeve 18 can be made of a number of materials including polyethylene terephthalate (PET). As shown in FIG. 2, the tubular balloon 16 defines a longitudinal axis 17.

Further, FIG. 2 indicates that the tubular sleeve 18 surrounds a substantial portion of the balloon 16, and that a plurality of dispensers 20 are mounted onto the tubular sleeve 18. Of these, the number of dispensers 20 illustrated is only exemplary. Importantly for the present method, all dispensers 20 are positioned in a single plane 19 that, as shown, is oriented substantially normal to the longitudinal axis 17. Also, it is preferable for the present method that the dispensers 20 be equally spaced around the axis 17.

A more complete appreciation of the structural cooperation between the balloon 16, the tubular sleeve 18 and the dispensers 20 is provided by FIG. 3A wherein, it will be seen that a distal end 22 of tubular sleeve 18 is attached directly to an outer surface 25 of balloon 16. By cross-referencing FIGS. 2 and 3A it can be seen that the tubular sleeve 18 substantially surrounds and encloses the balloon 16 and that a proximal end 24 of tubular sleeve 18 extends proximally from and beyond the balloon 16 over catheter 14. The tubular sleeve 18 cooperates with the outer surface 25 of the balloon 16 to define a portion of a fluid passageway 26. The proximal end 24 can be connected to an outer lumen 27 (not shown in FIG. 3A) of the catheter 14 to complete the fluid passageway 26.

FIG. 3A further shows that the distal end 28 of balloon 16 is affixed to the catheter 14, and that the proximal end 30 of the balloon 16 attaches onto the catheter 14 to create an inflation chamber 32 in the interior of the balloon 16. A balloon port 34 provides fluid access into the inflation chamber 32. For purposes of the present invention, the balloon port 34 can be connected in fluid communication with a balloon lumen (not shown) of the catheter 14. FIG. 3A also shows that catheter 14 is formed with an inner lumen 36 which is dimensioned to receive a guidewire 38 therethrough.

Figure 3B:
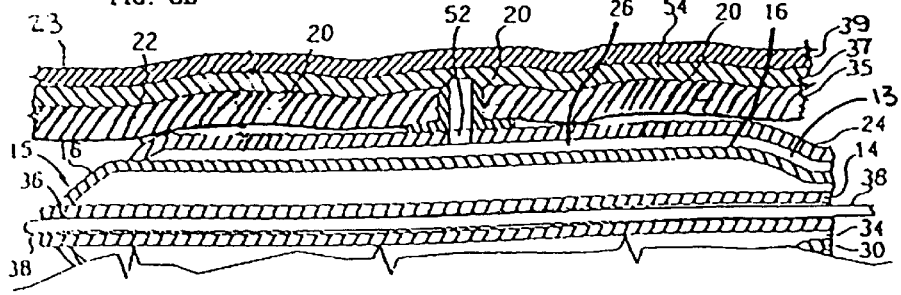
FIG. 3B is a cross-sectional view of an artery showing a dispenser positioned for release of a fluid medicament in the media layer of the artery.

As discussed previously, the wall 23 of the blood vessel 11 includes multiple layers. To facilitate the present discussion, some of the layers, namely, the intima layer 35, the media layer 37, and the adventitia layer 39 are illustrated in FIG. 1B and again in FIG. 3B. Importantly, when the device 10 is used in accordance with the present method, the depth of penetration of each dispenser 20 can be precisely controlled by controlling the length 41 (shown in FIG. 5A) of each dispenser 20. In accordance with the method of the present invention, the dispensers 20 extend a length 41 of between approximately 0.005 inches and approximately 0.02 inches from the tubular sleeve 18 when the balloon 16 is inflated. However, those skilled in the pertinent art will recognize that these distances are merely exemplary. Thus, the device 10 is able to deliver the fluid medicament 13 to a desired, target layer in the wall 23 of the blood vessel 11. For example, as illustrated in FIG. 3B, the dispenser 20 penetrates through the intima layer 35 and precisely delivers the fluid medicament 13 to the media layer 37, i.e. the target layer in this example. It is to be appreciated that a shorter dispenser 20 could be utilized to deliver the fluid medicament 13 to the intima layer 35. Additionally, in accordance with the method of the present invention, the device 10 can be used to simultaneously release the fluid medicament 13 within a target layer and dilate the lumen 21 of the blood vessel 11.

Referring now to FIG. 4A, each dispenser 20 includes a base plate 40 and a tubular protrusion 42 having an attachment end 44 and a penetrating section 46. Further, it is seen that the attachment end 44 of the tubular protrusion 42 affixes to and is an integral part of the base plate 40. Preferably, the dispenser 20 is made of nickel and the tubular protrusion 42 is formed by punching out the base plate 40. In the dispenser embodiment illustrated in FIG. 4A, the penetrating section 46 is defined by an opening which is opposite the base plate 40. The tubular protrusion 42 defines a fluid channel 48 which extends through the dispenser 20.

The penetrating section 46 of the dispenser 20 shown in FIG. 4A is substantially annular shaped.

FIG. 4B shows another embodiment of the dispenser 20. In this embodiment, each tubular protrusion 42 is substantially conical shaped as shown in FIG. 4B. Like the embodiment shown in FIG. 4A, the dispenser 20 shown in FIG. 4B is preferably made of nickel and is formed with a fluid channel 48 which extends through the dispenser 20.

FIGS. 5A, 5B and 5C illustrate additional, alternative embodiments of the dispenser 20. In the embodiments illustrated in FIGS. 5A, 5B and 5C, the tubular protrusion 42 is substantially conical shaped. However, in FIG. 5A, the penetrating section 46 is defined by an opening which extends through the side of the tubular protrusion 42. Somewhat similarly, in FIG. 5B, the penetrating section 46 is defined by a pair of openings which extend through the side of each tubular protrusion 42. This feature inhibits plugging of the penetrating section 46 during insertion into the wall 23 of the blood vessel 11. In FIG. 5C, the tubular protrusion 42 is made of a porous material. Thus, the porous material defines the penetrating section 46 of each dispenser 20. In the embodiment shown in FIG. 5C, the fluid medicament 13 is forced through the pores 49 of the porous tubular protrusion 42.

Referring now to FIG. 3A, the dispensers 20 are mounted on the tubular sleeve 18 so that the fluid channel 48 of each respective dispenser 20 is aligned with a hole 52 in the tubular sleeve 18. This is done to establish fluid communication between the particular dispenser 20 and the fluid passageway 26. As a practical matter, it may be preferable in the construction of the device 10 to first mount the dispenser 20 on the tubular sleeve 18, which can be done in any manner well known in the pertinent art, such as by bonding, and then piercing a hole 52 in the tubular sleeve 18 through the dispenser 20.

An alternative structure for a device 10 suitable for use in the present method is shown in FIG. 6. As shown, the alternative device 10 includes a multi-lumen catheter 14 formed to accommodate a guidewire 38, a balloon 16, a plurality of dispensers 20 and a plurality of tubular channels 64 mounted on the outer surface 25 of the balloon 16. Each tubular channel 64 has a smaller diameter than the balloon 16 and is positioned to be substantially parallel with a longitudinal axis 65 of the balloon 16.

FIG. 6 further shows that mounted on the surface of each tubular channel 64 is a dispenser 20. The dispensers 20 are positioned on the surface of tubular channel 64 so that when balloon 16 is inflated, the dispensers 20 move outwardly from the longitudinal axis 65 in a radial direction. Importantly for the present method, all dispensers 20 are positioned in a single plane 67 that is oriented substantially normal to the longitudinal axis 65 of the balloon 16. Further, it is preferable for the present method that the dispensers 20 be equally spaced around the longitudinal axis 65.

Figure 7:
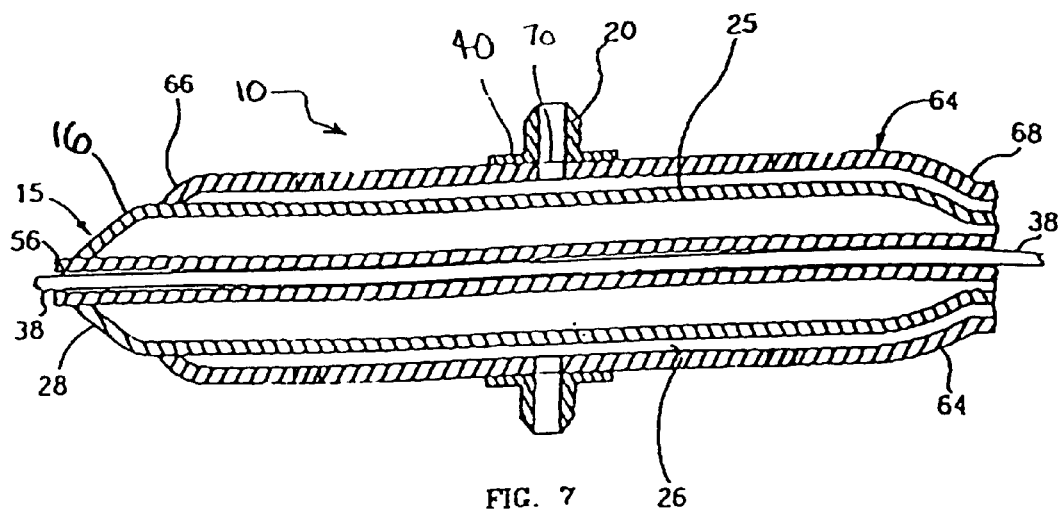
FIG. 7 is a cross-sectional view of the device shown in FIG. 6 as seen along line 7—7 in FIG. 6.

Referring now to FIG. 7, the cross-sectional view of the alternative device 10 shows the tubular channel 64 in more detail. More specifically, a distal end 66 of tubular channel 64 is sealed to create a portion of the fluid passageway 26 which connects the dispensers 20 to the fluid source 60. Referring to FIGS. 6 and 7, it is to be appreciated that the proximal end 68 of the tubular channel 64 is in fluid communication with the outer lumen 27 of the catheter 14. In turn, the outer lumen 27 is connected in fluid communication with the fluid pump 58 and the fluid medicament source 60.

Still referring to FIG. 7, the dispensers 20 are shown mounted on the surface of the tubular channel 64. As FIG. 7 further shows in detail, a base plate 40 of a dispenser 20 is mounted on the tubular channel 64 over a corresponding hole 70. From this view, it can be appreciated that any number of tubular channels 64 could be mounted on the external surface of balloon 16.

Figure 8:
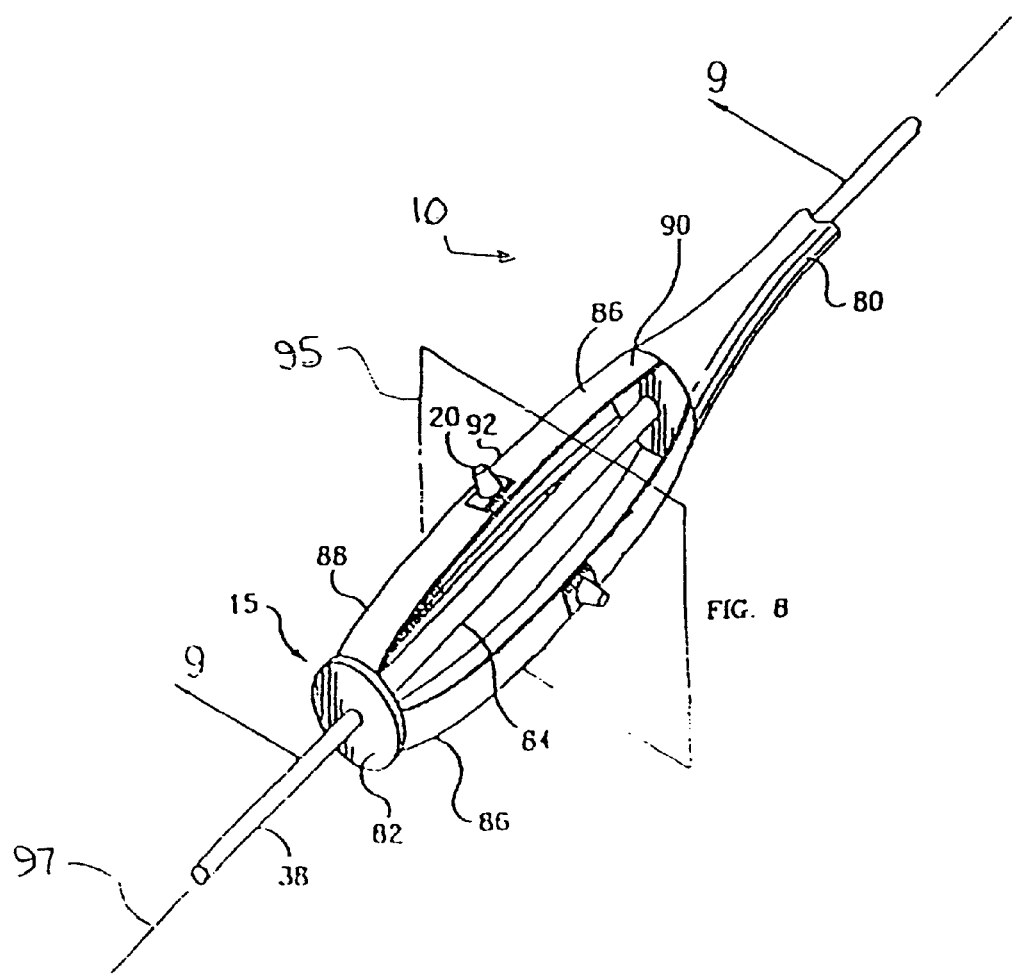
FIG. 8 is a perspective view of yet another embodiment of a device suitable for use in the present invention.

FIG. 8 shows yet another version of a device 10 suitable for the method of the present invention. In this version of the device 10, the expanding member 15 includes a multi-lumen catheter 80 and a grommet 82. Both the multi-lumen catheter 80 and the grommet 82 are disposed about the same longitudinal axis 97 with the grommet 82 positioned distally, and separated from, the distal end 88 of the multi-lumen catheter 80.

A mechanism is provided to move the grommet 82 translationally along the longitudinal axis 97. For example, referring to FIG. 8, a push-pull wire 84, is shown connected to the grommet 82. The push-pull wire 84 extends through one of the lumens of the multi-lumen catheter 80 allowing the push-pull wire 84 to move translationally in line with the longitudinal axis 97. The translational movement of the push-pull wire 84 causes the grommet 82 to undergo a similar translational displacement. Further, this version of the device 10 can be used in combination with the guidewire 38, as shown in FIG. 8. Specifically, the push-pull wire 84 may be formed with an internal lumen, allowing the catheter 80 and push-pull wire 84 to pass over the guidewire 38.

In the version of the device 10 shown in FIG. 8, a plurality of hollow, flexible tubes 86 are attached between the grommet 82 and the multi-lumen catheter 80. Each of the flexible tubes 86 includes a distal end 88, a proximal end 90 and a central region 92. The proximal end 90 of each tube 86 is joined to the multi-lumen catheter 80. The distal end 88 of each tube 86 is joined to the grommet 82. Preferably, the tubes 86 are distributed radially around the multi-lumen catheter 80 and grommet 82 in a manner substantially as shown in FIG. 8.

Figure 9:
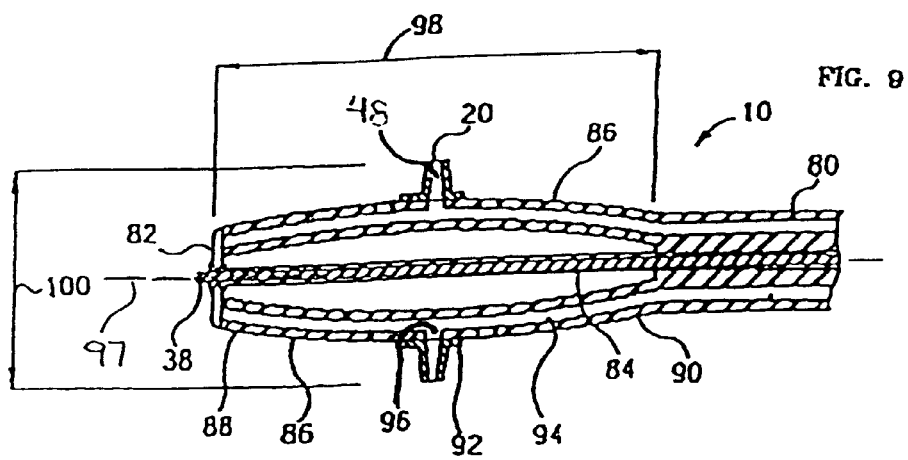
FIG. 9 is a cross-sectional view of the device of FIG. 8 shown in a retracted configuration, as seen along line 9—9 in FIG. 8.
Figure 10:
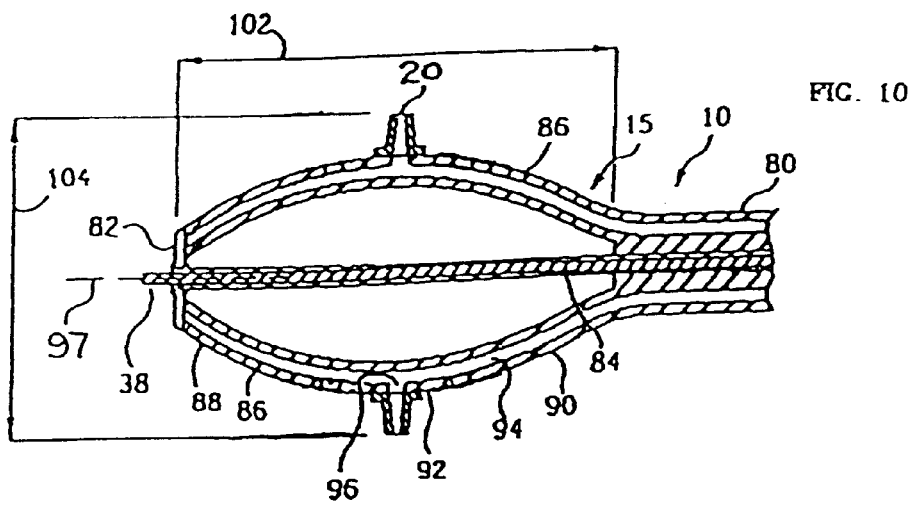
FIG. 10 is a cross-sectional view of the device of FIG. 8 shown in an expanded configuration, as seen along the line 9—9 in FIG. 8.
Figure 11:
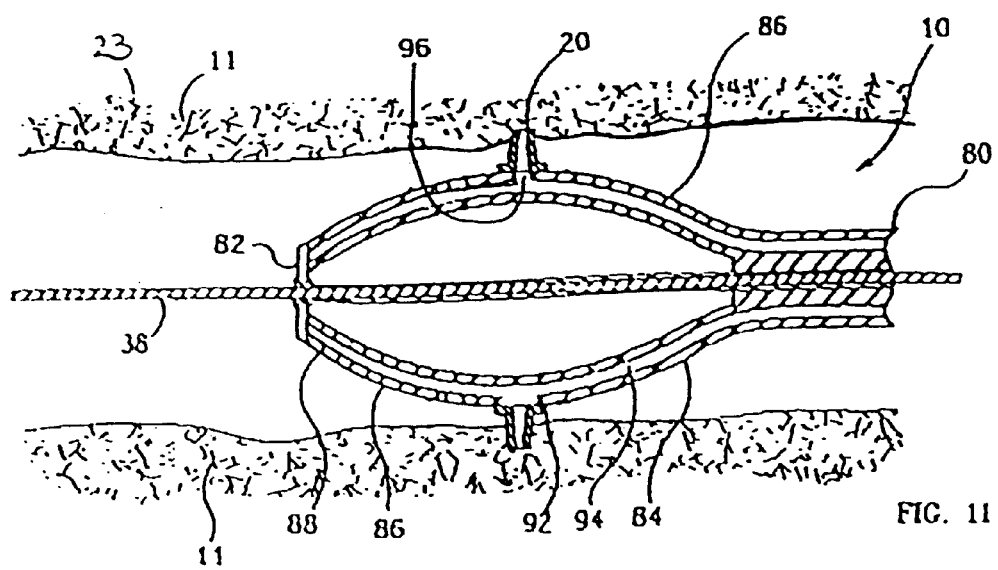
FIG. 11 is a cross-sectional view of the device of FIG. 8 positioned in the blood vessel of a patient.

Referring now to FIGS. 9–11, it may be seen that each flexible tube 86 is formed with a lumen 94. The lumen 94 of each flexible tube 86 passes through the multi-lumen catheter 80 allowing fluid medicament 13 to be passed through multi-lumen catheter 80 and into flexible tubes 86. The lumen 94 of each flexible tube 86 passes separately through multi-lumen catheter 80 allowing a different fluid medicament 13 to be passed into each flexible tube 86. Alternatively, the lumen 94 of each flexible tube 86 may be attached to one or more common lumens within the multi-lumen catheter 80.

Referring to FIGS. 8 and 9, it is shown that a dispenser 20 is attached to the central region 92 of each flexible tube 86. Each flexible tube 86 is formed with a hole 96 which correspond to a respective dispenser 20. Functionally, each hole 96 connects the fluid channel 48 of a respective dispenser 20 to lumen 94 allowing the fluid pump 58 to pump fluid medicaments 13 from the fluid source 60 into lumen 94 to be expelled through the dispensers 20. Importantly for the present method, all dispensers 20 are positioned in a single plane 95 oriented normal to the longitudinal axis 97 defined by the expanding member 15. Further, it is preferable for the present method that the dispensers 20 are equally spaced around the longitudinal axis 97.

Referring now to FIGS. 9 and 10, it is shown that the device 10 is movable between the first, contracted configuration (shown in FIG. 9) and the second, expanded configuration (shown in FIG. 10). Specifically, it may be seen that the grommet 82 and the multi-lumen catheter 80 are distanced by a first separation distance 98. The device 10 shown in FIG. 9 also has a first overall width designated 100. In comparison, the grommet 82 and the multi-lumen catheter 80 shown in FIG. 10 are distanced by a second separation distance 102 which is smaller than the first separation distance 98 of FIG. 9. The device 10, shown in FIG. 10 also has a second overall width 104 which is greater than the first overall width 100 shown in FIG. 9.

The movement between the first, contracted configuration shown in FIG. 9 and the second, expanded configuration shown in FIG. 10 is accomplished by the translational movement of the grommet 82 along the longitudinal axis 97. Specifically, as the push-pull wire 84 causes the grommet 82 to move towards the multi-lumen catheter 80, each of the flexible tubes 86 bows outwardly away from the longitudinal axis 97. In this manner, the push-pull wire 84 may be used to move the grommet 82 translationally to cause the flexible tubes 86 to alternately bow, as seen in FIG. 10, and straighten, as seen in FIG. 9. In some cases, it will be preferable to fabricate the flexible tubes 86 from a resilient material and shape the flexible tubes 86 to be initially biased in either a bowed or straight configuration.

Figure 12C:
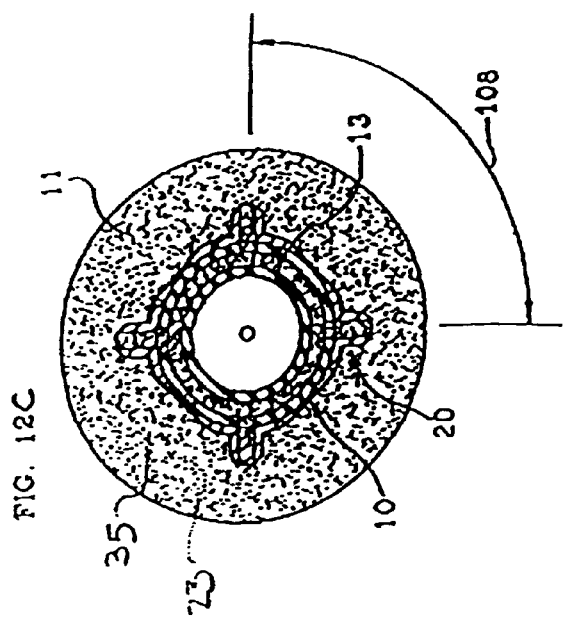
FIG. 12C is an axial cross-sectional view of the vessel and the device illustrating the dispensers penetrating the vessel wall.
Figure 12A:
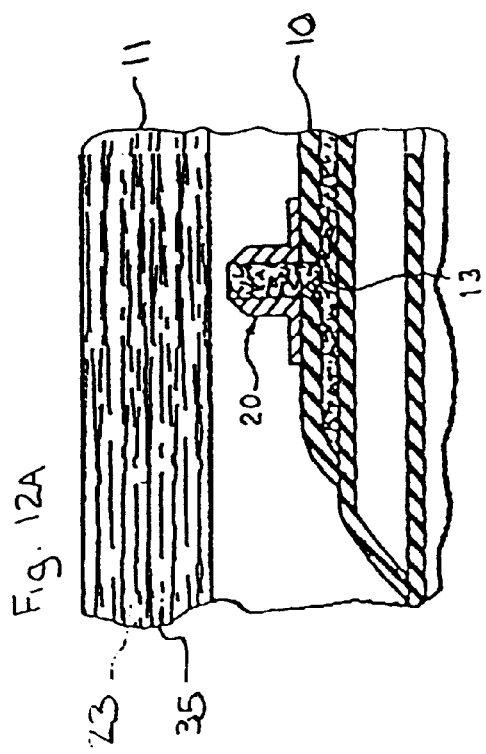
FIG. 12A is a longitudinal cross-sectional view of a portion of the vessel and a device prior to a dispenser penetrating the vessel wall.
Figure 12B:
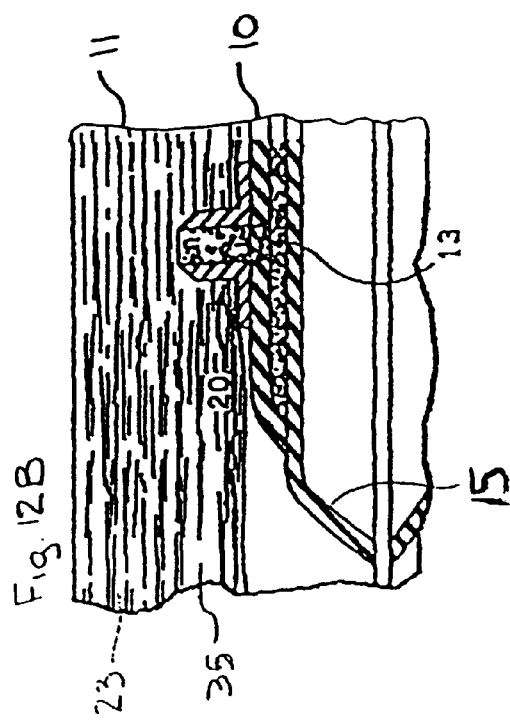
FIG. 12B is a longitudinal cross-sectional view of a portion of the vessel and a portion of the device after a dispenser penetrates the vessel wall.

FIGS. 12A–12F show the process whereby the fluid medicament 13 is pumped from each dispenser 20 into the intima layer 35 of an exemplary blood vessel 11 and then allowed to disperse. FIGS. 12A–12F further show that the fluid medicament 13 can be pumped into a target layer, in this case the intima 35, and allowed to disperse until a circumferential dispersion of fluid medicament 13 is achieved. First, as shown in FIG. 12A, the dispenser 20 is positioned adjacent to the target area of the blood vessel 11. Next, as shown in FIGS. 12B and 12C, the expanding member 15 is expanded, forcing the dispenser 20 to penetrate the target layer (in this case, the intima 35). Preferably, as illustrated in FIG. 12C, the dispensers 20 are circumferentially spaced to create a plurality of spaced apart medicinal deliveries 106. FIGS. 12D and 12E show the medicinal deliveries 106 which are confined to the intima layer 35. FIGS. 12F and 12G show the subsequent dispersion of the fluid medicament 13 around a circumference of the wall 23 of the blood vessel 11, creating a circumferential dispersion. The pumping rate required to achieve the desired circumferential dispersion depends upon the viscosity of the fluid medicament 13 utilized. Typically, between approximately 400 microliters and 700 microliters of the fluid medicament 13 is dispensed during a period of between approximately five and forty-five seconds to create the desired medicinal delivery 106 that will result in a circumferential dispersion. However, it should be recognized that the amounts and time frames provided herein are merely exemplary. It is also to be appreciated that the medicinal dispersion rate will be affected by the body's response (inflammation) to the tissue injury caused by the present method.

Further, the spacing required to create a plurality of spaced apart medicinal deliveries 106 which subsequently disperse the fluid medicament 13 along the treatment area 54 will also vary according to the fluid medicament 13 utilized. It is contemplated for the present method that the dispensers 20 are to be spaced a circumferential distance 108 of between approximately 1 millimeter and 6 millimeters, roughly 70 degrees and 140 degrees apart.

The composition of the fluid medicament 13 to be injected into the wall 23 of the blood vessel 11 depends upon the treatment being performed and the physical characteristics of the patient 12. More specifically, the fluid medicament 13 can be designed to treat a stenosis or disease de novo, inhibit a restenosis by minimizing the effects of a previous intravascular procedure and/or inhibit a stenosis in a blood vessel 11. For example, to inhibit a restenosis, the fluid medicament 13 can contain anti-proliferative agents which inhibit the proliferation of smooth muscle cell growth in the vessel in certain pathological conditions. These fluids selectively kill rapidly dividing cells and can be utilized to inhibit the proliferation of smooth tissue growth. Suitable fluids can include anti-proliferative agents such as methotrexate, prednisone, adriamycin, mitomycin C, protein synthesis inhibitors, toxin fragments such as pseudomonas exotoxin (PE) or Ricin A (RA) Toxin, and radioactive isotopes 112 such as $^{111}$Indium, $^{90}$Yttrium, $^{67}$Gallium, $^{99m}$Tc (Technetium 99), $^{205}$Thallium, and $^{32}$P (Phosphorous 32) radiopharmaceuticals. It is believed that the present method is uniquely suited to safely deliver toxic fluid medicaments 13 into the wall 23 of the blood vessel 11 while minimizing the amount of fluid medicament 13 which is washed away into the blood stream.

Alternatively, for example, a fluid medicament 13 which stimulates the production of collateral vessels can be delivered by the present method. These fluid medicaments 13 provide preventative treatment for the patient 12 by creating new collateral vessels in the event the original blood vessel 11 develops a stenosis. A fluid medicament 13 which includes an angiogenis factor can be utilized for this purpose.

Figure 13A:
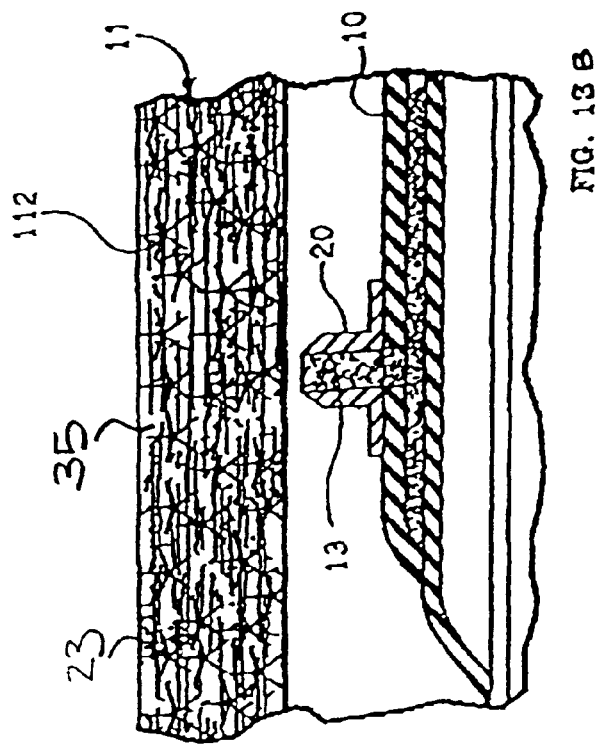
FIG. 13A is a longitudinal cross sectional view of the vessel and a device illustrating a fluid medicament containing a radioactive isotope being injected into the vessel wall.
Figure 13B:
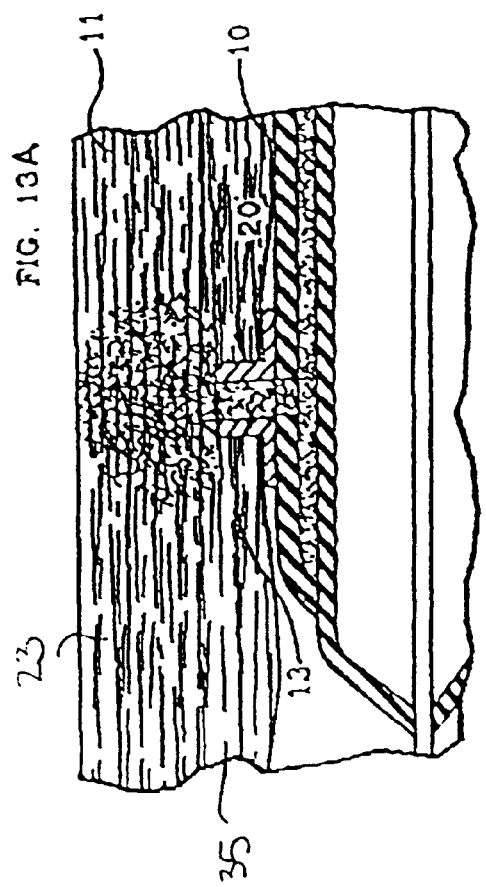
FIG. 13B is a longitudinal cross sectional view of a portion of the vessel and the device after a fluid medicament containing a radioactive isotope is injected into the vessel wall.

FIGS. 13A and 13B, illustrate the delivery and dispersion of a fluid medicament 13 that includes a radioactive isotope 112 which can reduce and inhibit tissue and/or cell growth of the wall 23 of the blood vessel 11. Because the radioactive isotopes 112 are injected directly in the wall 23 of the blood vessel 11 and are symmetrically injected around the circumference of the wall 23 of the blood vessel 11, relatively low energy radioactive isotopes 112 having a relatively short half life can be utilized. These relatively low energy radioactive isotopes 112 should cause minimal trauma to the patient 12. The present method provided herein is uniquely suited to safely deliver a radioactive isotope 112 to only the treatment area 54 of the wall 23 of the blood vessel 11, while minimizing the amount of radioactive isotope 112 which is washed away into the blood stream. Additionally, the radioactive isotope 112 can be encapsulated within a suitable carrier such as amino-mannose modified liposome, which is rapidly absorbed into the smooth muscle cells of the intima layer 35.

The exact dose of radiation to be delivered to the wall 23 of the blood vessel 11 can be varied to suit the needs of the patient 12. It is presently believed that a tissue absorbed dose of between approximately 8–40 Gray will be utilized to inhibit restenosis. The exact amount of fluid medicament 13 and type of fluid medicament 13 injected into the wall 23 of the blood vessel 11, can be varied to account for fluid medicament 13 washed into the blood stream and/or account for the active life of the fluid medicament 13.

Figure 14B:
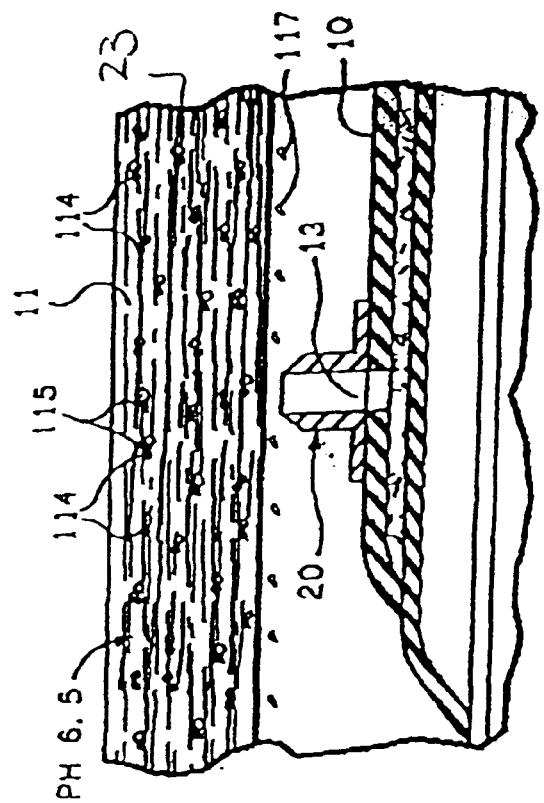
FIG. 14B is a longitudinal cross-sectional view of a portion of the vessel and the device after a portion of an injected fluid medicament precipitates within the vessel wall.
Figure 14A:
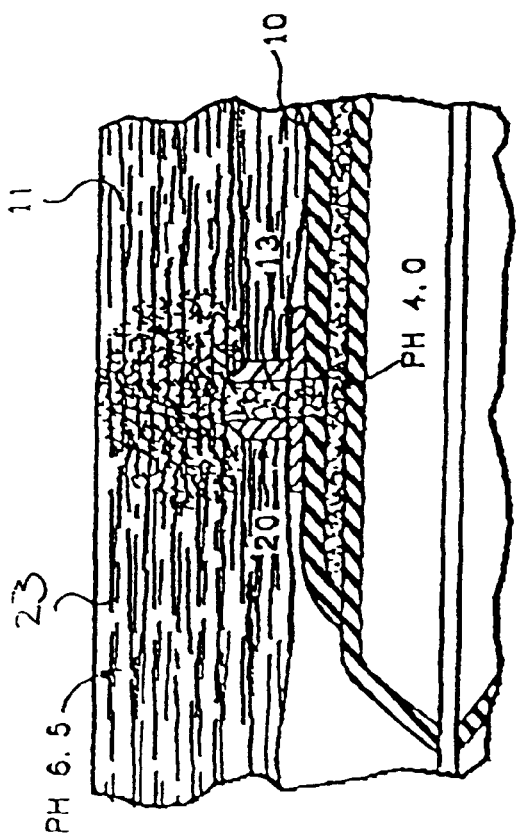
FIG. 14A is a longitudinal cross-sectional view of a portion of the vessel and the device after a fluid medicament containing a precipitant is injected into the vessel wall.

Referring to FIGS. 14A and 14B, it is shown that a precipitation process can be used to minimize the amount of fluid medicament 13 which is washed away into the blood stream. Specifically, a portion of the fluid medicament 13 can be precipitated at approximately the pH level of the wall 23 of the blood vessel 11. Typically, the vessel pH is approximately 7. A fluid medicament 13 containing a precipitator 114, and having a fluid pH level of less than approximately 6 or greater than approximately 8 can be utilized. After the fluid medicament 13 and precipitator 114 are dispensed into the wall 23 of the blood vessel 11, the fluid medicament pH level will approach 7, and a portion of the fluid medicament 13 may precipitate. For this embodiment, the fluid medicament 13 could include a precipitator 114, an active component 115 attached to or incorporated within the precipitator 114 and a carrier component 117 which carries the precipitator 114 and the active component 115. The active component 115 is the portion of the fluid medicament 13 which is designed to treat the patient 12. In this example, the precipitator 114 could precipitate in the wall 23 of the blood vessel 11 while the carrier component 117 gets washed away into the blood stream.

Because the active component 115 is attached to or incorporated within the precipitator 114, this ensures that the bulk of the active component 115 of the fluid medicament 13 remains in the wall 23 of the blood vessel 11 and minimizes the amount of the active component 115 of the fluid medicament 13 which is washed away into the blood stream. In this embodiment, the active component 115 of the fluid medicament 13, for example, can include an anti-proliferative agent as outlined above. Alternatively, the precipitator 114 and the active component 115 can be a radionuclide or radiopharmaceutical precipitate, such as gold colloidal, i.e. $^{198}$Au and $^{199}$Au, and/or an inorganic precipitate such as organo-metallic precipitate.

Additionally, the active component 115 of the fluid medicament 13 can be designed to have a slow, time-release formulation so that active component 115 is released to the wall 23 of the blood vessel 11 over an extended period of time. Stated another way, the active component 115 can biodegrade slowly over a period of time to release the active component of fluid medicament 13 into the wall 23 of the blood vessel 11 over an extended period of time. A biodegradable polymer may be used to provide a control release formulation to the active component 115.

Figure 15A:
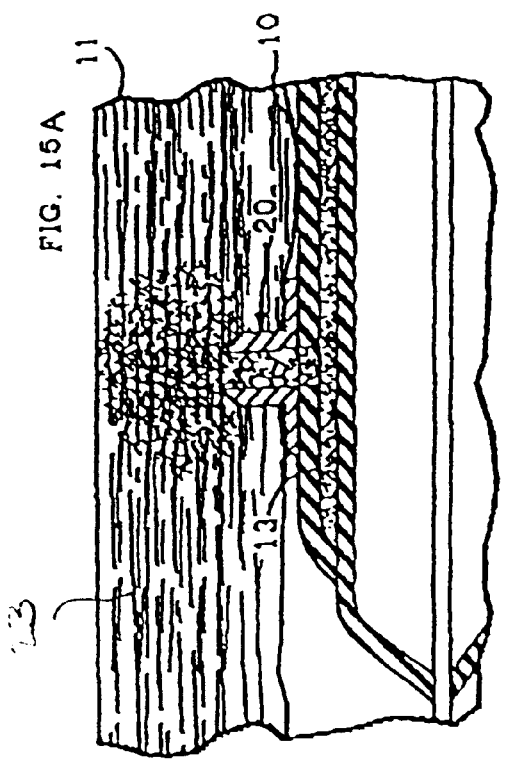
FIG. 15A is a longitudinal cross-sectional view of a portion of the vessel and the device after a fluid medicament with a binder has been injected into the vessel wall.

Alternatively, referring to FIGS. 15A and 15B, the fluid medicament 13 may include a binder 116, the active component 115 and the carrier component 117. The binder 116 is secured to the active component 115 of the fluid medicament 13. The binder 116 is adapted to bind, attach and/or crosslink to at least a portion of the wall 23 of the blood vessel 11. For example, the binder 116 could include a ligand which binds to a portion of the wall 23 of the blood vessel 11 such as collagen or the smooth muscle cell component of the wall 23 of the blood vessel 11. Because the binder 116 is secured to the active component 115, this ensures that the bulk of the active component 115 of the fluid medicament 13 remains in the wall 23 of the blood vessel 11 and minimizes the amount of the active component 115 of the fluid medicament 13 which is washed away into the blood stream. Examples of ligands capable of binding to the arterial wall components include PDGF receptors, adhesive molecules including, but not limited to certain molecules of the integrin family, and receptors on activated platelets such as thrombin receptors. Another suitable type of ligand is sold under the name CERETEC® by Amersham located in Arlington Heights, Ill. Alternatively, for example, phosphorous tridentate which binds to collagen can be utilized. In yet an alternative embodiment, the binder 116 can have a direct affinity to form ionic bonds, covalent bonds or Van der Waal attractions with the wall 23 of the blood vessel 11 or some component thereof.

Figure 16B:
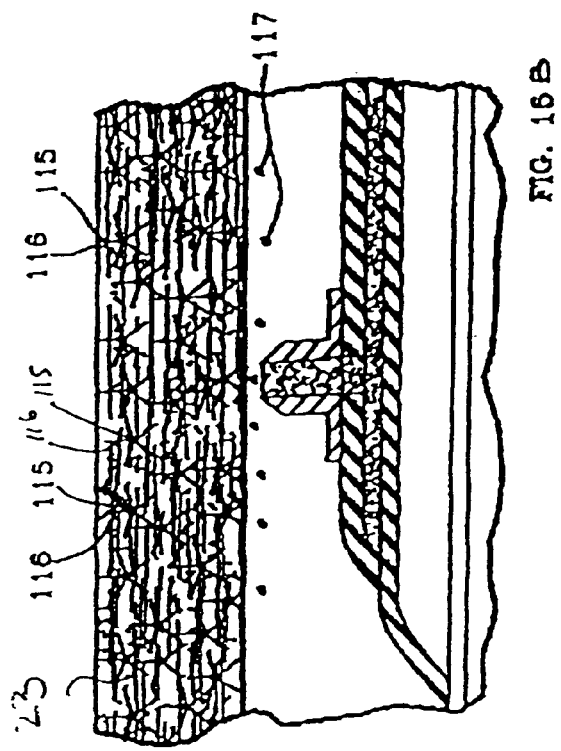
FIG. 16B is a longitudinal cross-sectional view of a portion of a vessel and device illustrating the vessel after a fluid medicament that includes a virus gene is injected into the wall of the vessel by the device.

Alternatively, as illustrated in FIGS. 16A–16C, the fluid medicament 13 can be used for gene therapy on the wall 23 of the blood vessel 11. In this embodiment, the fluid medicament 13 can include a suitable viral vector 118 which is adapted to infect a cell 120 and replace, modulate, inhibit or enhance one of the cell genes 122 within the cell 120. For example, the fluid medicament 13 could include a retroviral, adenoviral vectors or Adenovirus Associated Vectors (AAV) carrying the appropriate DNA payload for appropriate gene switching. Alternatively, for example, naked DNA or polycation-condensed DNA could be utilized for gene therapy. The method of the present invention allows for the use of fluid medicaments 13 which genetically alter the treatment area 54 of the wall 23 of the blood vessel 11 without effecting the rest of the body.

Still other fluid medicaments 13 which could be utilized with the method of the present invention include antibodies such as receptor site monoclonal antibodies, a toxic agent such as saponin, a genetic material such as DNA, a cellular material such as endothelial cells and/or medicaments such as heparin. The examples provided herein are merely examples of fluid medicaments 13 which may be useful with the present invention. Those skilled in the art will recognize that additional fluid medicaments 13 will be developed as medical technology improves. Additionally, those skilled in the art will recognize that the present invention can be utilized for applications other than inhibiting a restenosis. For example, with extended dispensers 20, the method of the present invention could deliver fluid medicaments 13 from the blood vessel 11 to specific organs.

OPERATION

An example of the operation of the balloon 16 version of the expanding member 15 can best be visualized with initial reference to FIGS. 1–3. First, the guidewire 38 is positioned into the blood vessel 11 of the patient 12. This is done to establish a mechanical pathway through the blood vessel 11 to the treatment area 54 where the fluid medicament 13 is to be released.

Next, the balloon 16, which is attached to the catheter 14, is moved over the guidewire 38 to the treatment area 54. The balloon 16 is at its first configuration during movement over the guidewire 38 in the blood vessel 11. Once the balloon 16 is properly positioned proximate the treatment area 54, an inflator 56 is activated to inflate the balloon 16 to its second configuration. As shown in FIG. 2, the inflator 56 is connected to the proximal (extracorporeal) end 29 of the catheter 14.

Referring back to FIGS. 3A and 3B, it will be appreciated that, as the balloon 16 is inflated, the expanding balloon 16 urges against the tubular sleeve 18 and causes the tubular sleeve 18 to likewise expand. Consequently, the dispensers 20 mounted on the tubular sleeve 18 move radially from the longitudinal axis 17 and embed into the treatment area 54. Further, the balloon 16 can be used to simultaneously dilate the lumen 21 of the blood vessel 11.

With the dispensers 20 embedded into the treatment area 54, the fluid pump 58 shown in FIG. 2 is activated to pump a fluid medicament 13 from the fluid medicament source 60 into the fluid passageway 26. Importantly, this pumping action also causes any fluid medicament 13 which has already been pumped into the fluid passageway 26 to be expelled through the fluid channels 48 of dispensers 20 and into the tissue of treatment area 54.

Alternatively, the fluid pump 58 could be activated prior to embedding the dispensers 20 into the wall 23 of the blood vessel 11 and a valve 62 could be used to prevent the flow of fluid medicament 13 until the dispensers 20 are embedded in the treatment area 54. The valve 62 can then be opened when the dispensers 20 penetrate into the treatment area 54 so that injection occurs substantially simultaneously with the embedding of the dispensers 20 in the treatment area 54. Alternatively, the injection of the fluid medicament 13 could happen after a time delay by waiting to open the valve 62 for at least about one second to about twenty seconds. Further, one or more fluid medicaments 13 can be released at different time intervals in the wall 23 of the blood vessel 11.

After the fluid medicament 13 from the fluid medicament source 60 has been dispensed into the treatment area 54, the balloon 16 can be deflated to the first configuration by reversing the inflator 56. This action will cause the balloon 16 to collapse and withdraw the dispensers 20 from the treatment area 54. The entire device 10 can then be withdrawn from the patient 12 over the guidewire 38.

The embodiment shown in FIG. 6 utilizes a plurality of individual, tubular channels 64. With this embodiment, it is possible to either maintain fluid communication with, or fluid isolation between, each tubular channel 64. For example, fluid communication between each tubular channel 64 can be established by fluidly connecting each tubular channel 64 together within one outer lumen 27 of the catheter 14 so that each tubular channel 64 is supplied fluid medicament 13 from the same fluid pump 58. Alternatively, fluid isolation may be maintained between each tubular channel 64 by providing each tubular channel 64 with a corresponding and independent outer lumen 27 and establishing its own fluid connection to a corresponding and independent fluid pump 58. Consequently, it is possible to inject a variety of alternate fluid medicaments 13 simultaneously by using a plurality of tubular channels 64 which are each connected to a separate fluid pump 58.

While the particular Method for Delivering Medication Into an Arterial Wall for Prevention of Restenosis as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A method for releasing fluid medicaments into a vessel wall of a patient at a treatment site, the method comprising the steps of:
    providing an expanding member defining an axis and having a plurality of dispensers mounted on said expanding member for movement therewith, said dispensers having one or more side openings being positioned in a plane oriented substantially perpendicular to said axis;
    advancing said expanding member through the vessel to the site;
    moving said expanding member between a first configuration wherein said dispensers are positioned substantially adjacent said axis of said expanding member, and a second configuration wherein said dispensers are radially extended from said axis for penetrating into the vessel wall; and
    providing a fluid medicament and releasing said fluid medicament through said side openings of said dispensers into the vessel wall for a substantially circumferential dispersion of said fluid medicament into said vessel wall.

2. The method of claim 1 wherein said fluid medicament inhibits the proliferation of smooth tissue growth in the vessel.

3. The method of claim 1 wherein said fluid medicament comprises a radioactive isotope.

4. The method of claim 1 wherein said fluid medicament stimulates the production of collateral vessels.

5. The method of claim 1 wherein said fluid medicament comprises $^{99m}$Tc (Technetium 99).

6. The method of claim 1 wherein said fluid medicament comprises a binder which binds to at least a portion of the vessel wall.

7. The method of claim 1 wherein said fluid medicament comprises $^{32}$P(Phosphorous 32).

8. The method of claim 1 wherein said fluid medicament comprises a gene for gene therapy.

9. The method of claim 1 wherein the dispensers are substantially conical.

10. A method for releasing fluid medicaments into a vessel wall of a patient at a treatment site, the method comprising the steps of:
    providing an expanding member defining an axis and having a plurality of dispensers mounted thereon for movement therewith, said dispensers having one or more side openings
    advancing said expanding member through the vessel to the site;
    moving said expanding member between a first configuration wherein said dispensers are positioned substantially adjacent said axis of said expanding member, and a second configuration wherein said dispensers are radially extended from said axis for penetrating into the vessel wall; and
    providing a fluid medicament and releasing a fluid medicament through said side openings of said dispensers into the vessel wall for dispersion of said fluid medicament into said vessel wall.

11. The method of claim 10 wherein the vessel wall is an artery having an intima layer.

12. The method of claim 11 wherein said fluid medicament inhibits the proliferation of smooth tissue growth in the vessel.

13. The method of claim 11 wherein said fluid medicament comprises a radioactive isotope.

14. The method of claim 11 wherein said fluid medicament stimulates the production of collateral vessels.

15. The method of claim 11 wherein said fluid medicament comprises $^{99m}$Tc (Technetium 99).

16. The method of claim 11 wherein said fluid medicament comprises a binder which binds to at least a portion of the vessel wall.

17. The method of claim 11 wherein said fluid medicament comprises $^{32}$P(Phosphorous 32).

18. The method of claim 11 wherein said fluid medicament comprises a gene for gene therapy.

19. The method of claim 10 wherein the dispensers are substantially conical.

20. A method for releasing fluid medicaments into a vessel wall of a patient at a treatment site, the method comprising the steps of:
    providing an expanding member defining an axis, and having a plurality of dispensers mounted thereon for movement therewith, said dispensers being made of a porous material;
    advancing said expanding member through the vessel to the site;

moving said expanding member between a first configuration wherein said dispensers are positioned substantially adjacent said axis of said expanding member, and a second configuration wherein said dispensers are radially extended from said axis for penetrating into the vessel wall; and providing a fluid medicament and releasing a fluid medicament through said dispensers into the vessel wall for dispersion of said fluid medicament into said vessel wall.

21. The method of claim 20 wherein said fluid medicament inhibits the proliferation of smooth tissue growth in the vessel.

22. The method of claim 20 wherein said fluid medicament comprises a radioactive isotope.

23. The method of claim 20 wherein said fluid medicament stimulates the production of collateral vessels.

24. The method of claim 20 wherein said fluid medicament comprises $^{99m}$Tc (Technetium 99).

25. The method of claim 20 wherein said fluid medicament comprises a binder which binds to at least a portion of the vessel wall.

26. The method of claim 20 wherein said fluid medicament comprises $^{32}$P(Phosphorous 32).

27. The method of claim 20 wherein said fluid medicament comprises a gene for gene therapy.

28. The method of claim 20 wherein the dispensers are substantially conical.

* * * * *

UNITED STATES PATENT AND TRADEMARK OFFICE
CERTIFICATE OF CORRECTION

PATENT NO. : 6,695,830 B2  Page 1 of 1
APPLICATION NO. : 09/778594
DATED : February 24, 2004
INVENTOR(S) : Vigil et al.

It is certified that error appears in the above-identified patent and that said Letters Patent is hereby corrected as shown below:

Col. 15, lines 54-55, change:
"having one or more side openings being positioned in a plane oriented substantially"
to
--having a first end, a second end, and one or more side openings located between the first end and the second end, said dispensers being positioned in a plane oriented substantially--

Col. 16, lines 26-27, change:
"having one or more side openings"
to
--having a first end, a second end, and one or more side openings located between the first end and the second end;--

Signed and Sealed this

Third Day of October, 2006

JON W. DUDAS
*Director of the United States Patent and Trademark Office*